United States Patent
Malek

(10) Patent No.: US 8,486,113 B2
(45) Date of Patent: Jul. 16, 2013

(54) SPINAL STABILIZATION SYSTEMS

(76) Inventor: Michel H. Malek, Chicago, IL (US)

( * ) Notice: Subject to any disclaimer, the term of this patent is extended or adjusted under 35 U.S.C. 154(b) by 174 days.

(21) Appl. No.: 12/982,476

(22) Filed: Dec. 30, 2010

(65) Prior Publication Data
US 2011/0160774 A1  Jun. 30, 2011

Related U.S. Application Data

(63) Continuation of application No. 10/722,119, filed on Nov. 25, 2003, now Pat. No. 7,862,586.

(51) Int. Cl.
*A61B 17/70* (2006.01)

(52) U.S. Cl.
USPC .................................................. 606/264

(58) Field of Classification Search
USPC ............. 606/246, 250, 256, 257, 259–261, 606/264, 265, 279; 623/17.11, 17.16, 23.47; 403/52, 119, 120, 122, 361
See application file for complete search history.

(56) References Cited

U.S. PATENT DOCUMENTS

| | | | |
|---|---|---|---|
| 2,490,364 A | 12/1949 | Livingston | |
| 4,011,602 A | 3/1977 | Rybicki et al. | |
| 4,349,921 A | 9/1982 | Kuntz | |
| 4,401,112 A | 8/1983 | Rezaian | |
| 4,643,178 A | 2/1987 | Nastari et al. | |
| 4,657,550 A | 4/1987 | Daher | |
| 4,743,256 A | 5/1988 | Brantigan | |
| 4,743,260 A | 5/1988 | Burton | |
| 4,759,766 A | 7/1988 | Buettner-Janz et al. | |
| 4,759,769 A | 7/1988 | Hedman et al. | |
| 4,863,476 A | 9/1989 | Shepperd | |
| 4,946,378 A | 8/1990 | Hirayama et al. | |
| 4,946,458 A | 8/1990 | Harms et al. | |
| 4,950,270 A | 8/1990 | Bowman et al. | |
| 4,997,432 A | 3/1991 | Keller | |
| 5,024,670 A | 6/1991 | Smith et al. | |
| 5,084,048 A | 1/1992 | Jacob et al. | |
| 5,092,866 A | 3/1992 | Breard et al. | |
| 5,122,130 A | 6/1992 | Keller | |
| 5,246,458 A | 9/1993 | Graham | |
| 5,258,031 A | 11/1993 | Salib et al. | |
| 5,261,911 A | 11/1993 | Carl | |

(Continued)

FOREIGN PATENT DOCUMENTS

| | | |
|---|---|---|
| DE | 22 63 842 A | 7/1974 |
| DE | 30 23 353 A1 | 4/1981 |

(Continued)

OTHER PUBLICATIONS

"Anatomic Facet Replacement System (AFRS™)," Natural Motion; published by Facet Solutions, Inc.; http://www.facetsolutions.com/Device.html on or before Nov. 2, 2007, 1 page.

(Continued)

*Primary Examiner* — Eduardo C Robert
*Assistant Examiner* — David Comstock
(74) *Attorney, Agent, or Firm* — Foley & Lardner LLP

(57) ABSTRACT

Spinal stabilizing elements and spinal stabilization systems composed of spinal stabilizing elements in combination with disc prostheses or disc nucleus replacements are provided. The stabilizing elements and stabilization systems are designed to preserve the natural mobility of vertebral discs and facet joints in patients with facet joint disease or patients who has undergone a prior destabilizing procedure, such as a facetectomy. The stabilizing elements may be pivoting elements or dynamic elements.

16 Claims, 12 Drawing Sheets

U.S. PATENT DOCUMENTS

| | | | |
|---|---|---|---|
| 5,282,863 A | 2/1994 | Burton |
| 5,306,310 A | 4/1994 | Siebels |
| 5,314,477 A | 5/1994 | Marnay |
| 5,314,478 A | 5/1994 | Oka et al. |
| 5,336,223 A | 8/1994 | Rogers |
| 5,352,224 A | 10/1994 | Westermann |
| 5,375,823 A | 12/1994 | Navas |
| 5,380,324 A | 1/1995 | Muller et al. |
| 5,380,328 A | 1/1995 | Morgan |
| 5,401,269 A | 3/1995 | Buttner-Janz et al. |
| 5,415,659 A | 5/1995 | Lee et al. |
| 5,437,671 A | 8/1995 | Lozier et al. |
| 5,458,641 A | 10/1995 | Ramirez Jimenez |
| 5,466,237 A | 11/1995 | Byrd et al. |
| 5,474,555 A | 12/1995 | Puno et al. |
| 5,496,318 A | 3/1996 | Howland et al. |
| 5,534,029 A | 7/1996 | Shima |
| 5,536,124 A | 7/1996 | Silva |
| 5,540,688 A | 7/1996 | Navas |
| 5,556,431 A | 9/1996 | Buttner-Janz |
| 5,562,738 A | 10/1996 | Boyd et al. |
| 5,591,166 A | 1/1997 | Bernhardt et al. |
| 5,607,425 A | 3/1997 | Rogozinski |
| 5,628,740 A | 5/1997 | Mullane |
| 5,645,596 A | 7/1997 | Kim et al. |
| 5,649,925 A | 7/1997 | Barbera Alacreu |
| 5,672,175 A | 9/1997 | Martin |
| 5,674,296 A | 10/1997 | Bryan et al. |
| 5,688,275 A | 11/1997 | Koros et al. |
| 5,702,453 A | 12/1997 | Rabbe et al. |
| 5,702,455 A | 12/1997 | Saggar |
| 5,713,899 A | 2/1998 | Marnay et al. |
| 5,725,582 A | 3/1998 | Bevan et al. |
| 5,776,198 A | 7/1998 | Rabbe et al. |
| 5,836,948 A | 11/1998 | Zucherman et al. |
| 5,882,226 A | 3/1999 | Bell et al. |
| 5,893,889 A | 4/1999 | Harrington |
| 5,951,553 A | 9/1999 | Betz et al. |
| 5,989,290 A | 11/1999 | Biedermann et al. |
| 6,019,792 A | 2/2000 | Cauthen |
| 6,030,389 A | 2/2000 | Wagner et al. |
| 6,063,121 A | 5/2000 | Xavier et al. |
| 6,074,390 A | 6/2000 | Zucherman et al. |
| 6,083,224 A | 7/2000 | Gertzbein et al. |
| 6,113,637 A | 9/2000 | Gill et al. |
| 6,123,711 A | 9/2000 | Winters |
| 6,139,579 A | 10/2000 | Steffee et al. |
| 6,146,421 A | 11/2000 | Gordon et al. |
| 6,179,874 B1 | 1/2001 | Cauthen |
| 6,214,012 B1 | 4/2001 | Karpman et al. |
| 6,217,578 B1 | 4/2001 | Crozet et al. |
| 6,228,118 B1 | 5/2001 | Gordon |
| 6,241,730 B1 | 6/2001 | Alby |
| 6,293,949 B1 | 9/2001 | Justis et al. |
| 6,296,644 B1 | 10/2001 | Saurat et al. |
| 6,296,664 B1 | 10/2001 | Middleton |
| 6,315,797 B1 | 11/2001 | Middleton |
| 6,368,350 B1 | 4/2002 | Erickson et al. |
| 6,375,682 B1 | 4/2002 | Fleischmann et al. |
| 6,375,683 B1 | 4/2002 | Crozet et al. |
| 6,395,034 B1 | 5/2002 | Suddaby |
| 6,402,750 B1 | 6/2002 | Atkinson et al. |
| 6,419,703 B1 | 7/2002 | Fallin et al. |
| 6,454,807 B1 | 9/2002 | Jackson |
| 6,478,800 B1 | 11/2002 | Fraser et al. |
| 6,500,178 B2 | 12/2002 | Zucherman et al. |
| 6,517,542 B1 | 2/2003 | Papay et al. |
| 6,517,580 B1 | 2/2003 | Ramadan et al. |
| 6,520,990 B1 | 2/2003 | Ray |
| 6,540,785 B1 | 4/2003 | Gill et al. |
| 6,554,831 B1 | 4/2003 | Rivard et al. |
| 6,565,605 B2 | 5/2003 | Goble et al. |
| 6,579,319 B2 | 6/2003 | Goble et al. |
| 6,579,320 B1 | 6/2003 | Gauchet et al. |
| 6,582,466 B1 | 6/2003 | Gauchet |
| 6,582,468 B1 | 6/2003 | Gauchet |
| 6,585,769 B1 | 7/2003 | Muhanna et al. |
| 6,607,558 B2 | 8/2003 | Kuras |
| 6,616,669 B2 | 9/2003 | Ogilvie et al. |
| 6,626,905 B1 | 9/2003 | Schmiel et al. |
| 6,626,908 B2 | 9/2003 | Cooper et al. |
| 6,652,585 B2 | 11/2003 | Lange |
| 6,685,742 B1 | 2/2004 | Jackson |
| 6,695,842 B2 | 2/2004 | Zucherman et al. |
| 6,730,126 B2 | 5/2004 | Boehm et al. |
| 6,752,831 B2 | 6/2004 | Sybert et al. |
| 6,761,720 B1 | 7/2004 | Senegas |
| 6,764,515 B2 | 7/2004 | Ralph et al. |
| 6,770,096 B2 | 8/2004 | Bolger et al. |
| 6,835,205 B2 | 12/2004 | Atkinson et al. |
| 6,852,128 B2 | 2/2005 | Lange |
| 6,902,566 B2 | 6/2005 | Zucherman et al. |
| 6,946,000 B2 | 9/2005 | Senegas et al. |
| 6,966,910 B2 | 11/2005 | Ritland |
| 6,966,931 B2 | 11/2005 | Huang |
| 6,989,011 B2 | 1/2006 | Paul et al. |
| 7,022,138 B2 | 4/2006 | Mashburn |
| 7,025,787 B2 | 4/2006 | Bryan et al. |
| 7,041,138 B2 | 5/2006 | Lange |
| 7,044,970 B2 | 5/2006 | Errico et al. |
| 7,056,343 B2 | 6/2006 | Schafer et al. |
| 7,101,375 B2 | 9/2006 | Zucherman et al. |
| 7,147,665 B1 | 12/2006 | Bryan et al. |
| 7,175,623 B2 | 2/2007 | Thramann et al. |
| 7,186,256 B2 | 3/2007 | Michelson |
| 7,201,751 B2 | 4/2007 | Zucherman et al. |
| 7,255,713 B2 | 8/2007 | Malek |
| 7,255,714 B2 | 8/2007 | Malek |
| 7,282,064 B2 | 10/2007 | Chin |
| 7,318,825 B2 | 1/2008 | Butler et al. |
| 7,402,176 B2 | 7/2008 | Malek |
| 2001/0016773 A1 | 8/2001 | Serhan et al. |
| 2001/0029375 A1 | 10/2001 | Betz et al. |
| 2001/0032020 A1 | 10/2001 | Besselink |
| 2001/0037111 A1 | 11/2001 | Dixon et al. |
| 2001/0051829 A1 | 12/2001 | Middleton |
| 2002/0022888 A1 | 2/2002 | Serhan et al. |
| 2002/0072679 A1 | 6/2002 | Schock et al. |
| 2002/0107574 A1 | 8/2002 | Boehm et al. |
| 2002/0111683 A1 | 8/2002 | Ralph et al. |
| 2002/0147454 A1 | 10/2002 | Neto |
| 2003/0009223 A1 | 1/2003 | Fehling et al. |
| 2003/0009226 A1 | 1/2003 | Graf |
| 2003/0018390 A1 | 1/2003 | Husson |
| 2003/0023312 A1 | 1/2003 | Thalgott |
| 2003/0032958 A1 | 2/2003 | Soubeiran |
| 2003/0055427 A1 | 3/2003 | Graf |
| 2003/0100951 A1 | 5/2003 | Serhan et al. |
| 2003/0149484 A1 | 8/2003 | Michelson |
| 2003/0176861 A1 | 9/2003 | Reed |
| 2003/0191534 A1 | 10/2003 | Viart et al. |
| 2003/0229348 A1 | 12/2003 | Sevrain |
| 2004/0002762 A1 | 1/2004 | Hawkins |
| 2004/0015172 A1 | 1/2004 | Biedermann et al. |
| 2004/0039371 A1 | 2/2004 | Tockman et al. |
| 2004/0133278 A1 | 7/2004 | Marino et al. |
| 2004/0153156 A1 | 8/2004 | Cohen et al. |
| 2004/0167626 A1 | 8/2004 | Geremakis et al. |
| 2005/0004673 A1 | 1/2005 | Kluger |
| 2005/0085910 A1 | 4/2005 | Sweeney |
| 2005/0113927 A1 | 5/2005 | Malek |
| 2005/0131536 A1 | 6/2005 | Eisermann et al. |
| 2005/0143823 A1 | 6/2005 | Boyd et al. |
| 2005/0165486 A1 | 7/2005 | Trieu |
| 2005/0209593 A1 | 9/2005 | Kolb |
| 2005/0209697 A1 | 9/2005 | Paponneau et al. |
| 2005/0234425 A1 | 10/2005 | Miller et al. |
| 2006/0036243 A1 | 2/2006 | Sasso et al. |
| 2006/0064099 A1 | 3/2006 | Pavlov et al. |
| 2006/0079895 A1 | 4/2006 | McLeer |
| 2006/0106381 A1 | 5/2006 | Ferree et al. |
| 2006/0161154 A1 | 7/2006 | McAfee |
| 2006/0190081 A1 | 8/2006 | Kraus et al. |
| 2006/0200140 A1 | 9/2006 | Lange |
| 2006/0224223 A1 | 10/2006 | Podhajsky et al. |
| 2006/0235390 A1 | 10/2006 | Zhang et al. |
| 2007/0010813 A1 | 1/2007 | Zucherman et al. |

| | | |
|---|---|---|
| 2007/0083265 A1 | 4/2007 | Malone |
| 2007/0112299 A1 | 5/2007 | Smit et al. |
| 2007/0173937 A1 | 7/2007 | Khalili |
| 2007/0250166 A1 | 10/2007 | McKay |
| 2007/0270828 A1 | 11/2007 | Bruneau et al. |
| 2008/0027444 A1 | 1/2008 | Malek |
| 2009/0036799 A1 | 2/2009 | Sandhu et al. |
| 2009/0062919 A1 | 3/2009 | Malek |
| 2009/0099601 A1 | 4/2009 | Aferzon et al. |
| 2009/0177233 A1 | 7/2009 | Malek |
| 2009/0204149 A1 | 8/2009 | Malek |
| 2009/0287118 A1 | 11/2009 | Malek |
| 2010/0121378 A1 | 5/2010 | Malek |
| 2010/0160964 A1 | 6/2010 | Malek |
| 2011/0054530 A1 | 3/2011 | Lins |

FOREIGN PATENT DOCUMENTS

| | | |
|---|---|---|
| EP | 0 176 728 A | 4/1986 |
| EP | 0 560 140 B1 | 9/1993 |
| EP | 0 560 141 A | 9/1993 |
| EP | 0 566 810 B1 | 10/1993 |
| FR | 2694882 A | 2/1994 |
| FR | 2801782 | 1/1999 |
| FR | 2805985 | 9/2001 |
| WO | WO-94/04100 | 3/1994 |
| WO | WO-95/26697 | 10/1995 |
| WO | WO-01/06939 | 2/2001 |
| WO | WO-02/24087 | 3/2002 |
| WO | WO 03/094699 | 11/2003 |
| WO | WO-2008/014337 | 1/2008 |
| WO | WO-2009/088746 | 7/2009 |
| WO | WO-2009/100117 | 8/2009 |

OTHER PUBLICATIONS

The International Search Report and Written Opinion for PCT/US2004/032116 mailed on Feb. 16, 2005, 12 pages.
European Patent Office Search Report for Application No. 04812086.9, dated Aug. 19, 2011, 5 pages.
Australian Office Action dated Nov. 25, 2009 received in Appln. No. 2004294954.
Final Office Action received for U.S. Appl. No. 10/722,119 DTD Apr. 2, 2008.
Final Office Action received for U.S. Appl. No. 10/722,119 DTD Mar. 26, 2010.
International Search Report and Written Opinion received for PCT/US04/39494 dated Jul. 7, 2005.
Non-final Office Action received for U.S. Appl. No. 10/722,119 DTD Oct. 4, 2007.
Non-final Office Action received for U.S. Appl. No. 10/722,119 DTD Sep. 2, 2009.
Notice of Allowance received for U.S. Appl. No. 10/722,119 DTD Jun. 30, 2010.
Office Action received in Japanese Appln. No. 2006-541692 dated May 17, 2010.

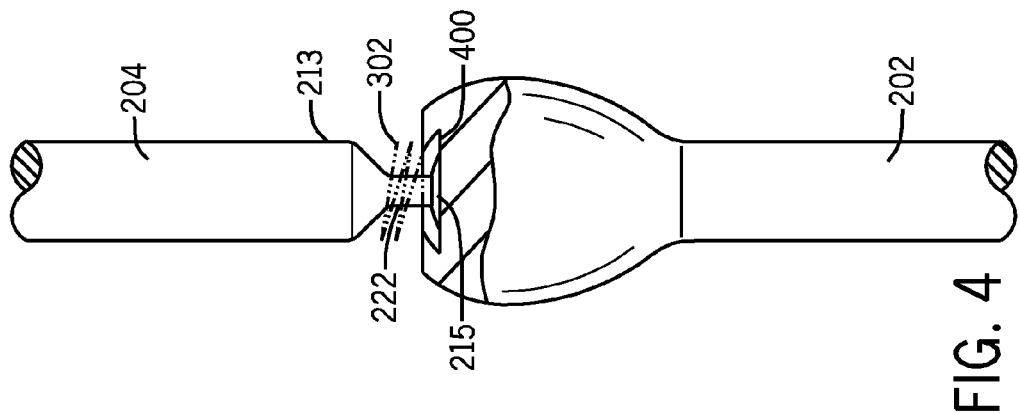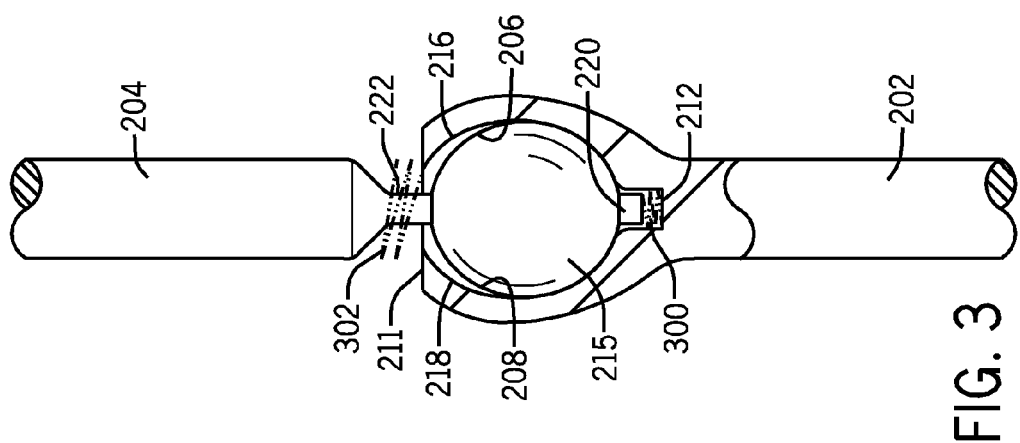

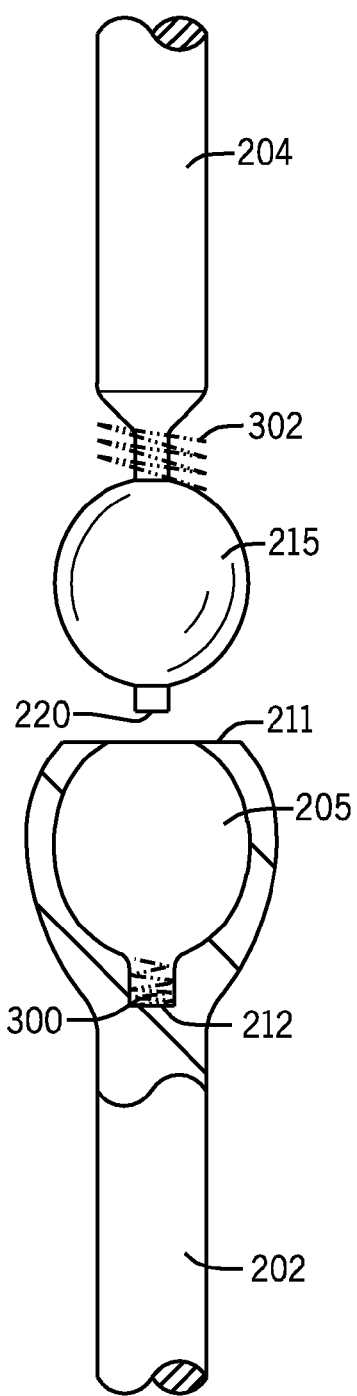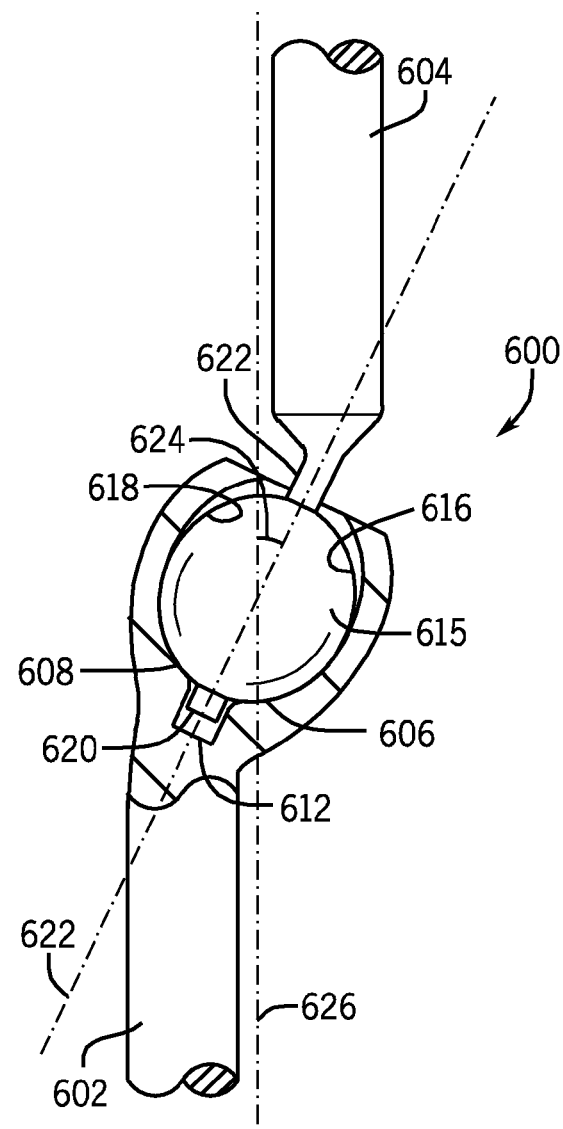
FIG. 5
FIG. 6

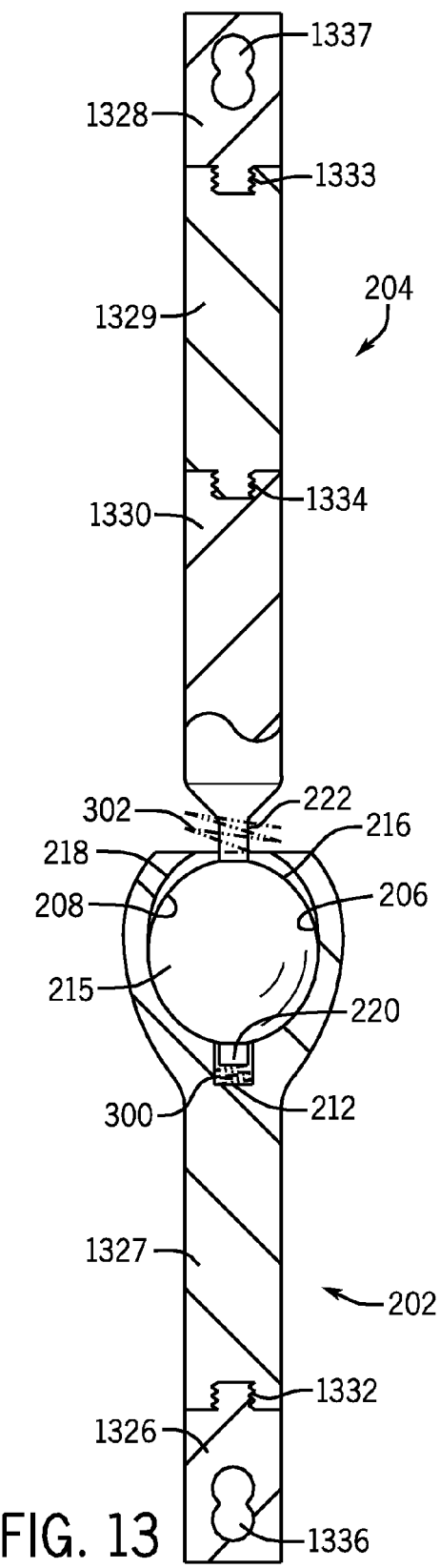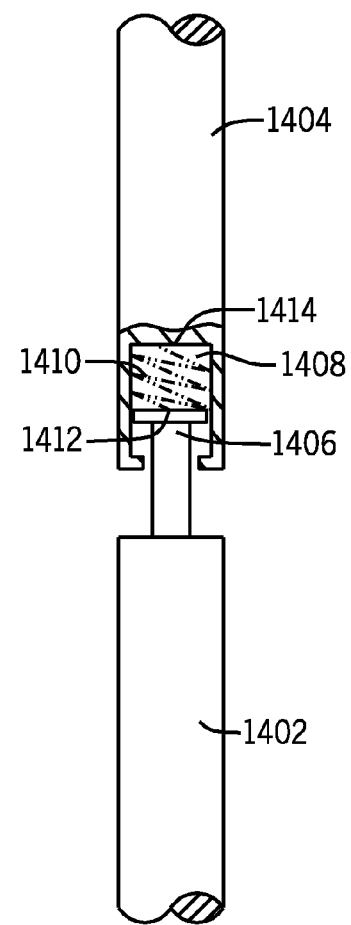
FIG. 13
FIG. 14

SPINAL STABILIZATION SYSTEMS

CROSS-REFERENCE TO RELATED PATENT APPLICATIONS

This application is a continuation of U.S. patent application Ser. No. 10/722,119, filed on Nov. 25, 2003, which is hereby incorporated by reference, in its entirety, for any and all purposes.

FIELD OF THE INVENTION

The present invention provides devices for the stabilization of the spinal column. In particular, the present invention provides spinal stabilizing elements and spinal stabilization systems that combine an intervertebral disc prosthesis with a variety of trans-vertebral stabilizing elements to retain, at least in part, the natural physiological degrees of motion of the spine.

BACKGROUND OF THE INVENTION

Degenerative disc disease, spinal trauma and tumors are common and painful conditions suffered by a significant portion of the population. In some instances, the pain and complications caused by these conditions may be bad enough to require that one or more vertebra, facet joints, and/or intervertebral discs be removed from the spinal column. In these instances, arthrodesis or bone fusion are common treatments used to facilitate the realignment and/or fixation of the spinal elements. Typically, two types of assemblies are known for securing one or more vertebra in order to obtain arthrodesis or bone fusion. The first type of assembly generally includes two posterior vertebral plates disposed longitudinally on either side of the spinous processes. Each plate is attached between adjacent vertebra using bone anchoring elements, such as bone screws. Together the plates provide a rigid vertebral fixation. The second type of stabilizing assembly generally includes two posterior vertebral rods disposed longitudinally on either side of the spinous processes. Like the plates, these rods are attached between adjacent vertebra using appropriate bone anchoring elements to provide a rigid vertebral fixation.

One drawback of rigid fixation derives from the fact that significant loads are placed on the stabilizing assemblies and particularly on the anchoring sites thereof. These loads may result in the loosening of the assembly from the vertebra or even the breaking of the assembly. The stabilizing assemblies are often supplemented with bone grafts formed from transplanted bone tissue and/or artificial fusion cages in order to fuse the adjacent vertebra. Unfortunately, such bone grafts and fusion can cause serious complications throughout the patient's life because fusing the vertebra subjects the remaining spinal elements to high stress and degeneration. This is particularly true of the remaining adjacent vertebra and vertebral discs because these elements must accommodate an even greater degree of motion. Moreover, spinal fusions limit the range of motion for patients in flexion, extension, rotation and lateral bending.

Similar assemblies are also used to correct spinal deformities, such as those associated with scoliosis, spinal traumas and tumors. In these systems correcting rods spanning two or more vertebra are typically implanted on either side of the spinous processes.

In addition to rigid spinal stabilization assemblies, some semi-rigid devices have been proposed. Some such devices are aimed at preserving a small amount of intervertebral elasticity in order to assist in subsequent bone fusion and to reduce stress. Other such devices provide stabilizing rods that are capable of sliding in a vertical direction with respect to the vertebra in order to accommodate spinal column growth.

Because of the problems associated with rigid vertebral fixation, the use of artificial disc prostheses has become an attractive option to many patients. These disc prostheses may be inserted in place of a natural vertebral disc in order to simulate at least some of the natural intervertebral movement and to restore proper disc height. Ideally, a disc prosthesis will operate in conjunction with the facet joints to restore the full range of motion of the spine. The facet joints are posterior vertebral elements that help to support axial, torsional and shear loads that act on the spinal column. When a facet joint becomes diseased or deformed (e.g. enlarged), it is sometimes necessary to remove part or all of the facet joint in a full or partial facetectomy. Unfortunately, the removal of the facet joint may destabilize the spinal column by decreasing the stiffness in flexion, extension, lateral bending and rotation. Moderate or advanced facet disease and facetectomies, or other prior destabilizing procedures, may be a contraindication for prosthetic discs.

Thus, a need exists for a spinal stabilization system that preserves at least some of the physiological mobility of the vertebra, vertebral discs, and facet joints after a prior destabilizing procedure, such as a facetectomy or laminectomy.

SUMMARY OF THE INVENTION

Spinal stabilizing elements and spinal stabilization systems are provided herein. The stabilization systems combine at least one disc prosthesis and/or at least one disc nucleus replacement with one or more stabilizing elements to retain or simulate at least some of the physiological intervertebral mobility of the spine by distributing the stress and mobility functions between the disc prosthesis or disc nucleus replacement and the stabilizing elements. Specifically, the systems provide a disc prosthesis or disc nucleus replacement capable of retaining or simulating at least one motion of a natural intervertebral disc while simultaneously providing a trans-vertebral stabilizing element capable of retaining or simulating at least one motion of a natural facet joint. In some embodiments, the stabilizing elements are capable of preserving or simulating flexion, extension, lateral bending, compression and rotation of the spine.

The stabilization systems include a trans-vertebral stabilizing element disposed outside of the intervertebral space between adjacent vertebrae in the spine to provide an intervertebral support. This element serves to bear a portion of the load on the spinal column while maintaining a degree of mobility between the adjacent vertebra.

One aspect of the invention provides a spinal stabilization system wherein the stabilizing element includes a first segment that is anchored to a first vertebra by a first connector and a second segment anchored to another vertebra by a second connector. The two segments are connected by a joint that provides the stabilizing element with at least one degree of motion, such as a rotation, a compression, an extension, a flexion and/or a bending motion. Suitable stabilizing elements include, but are not limited to, rods and plates.

The joint used to connect the segments of the stabilizing element may be any joint that is capable of providing a degree of motion between the two segments of the stabilizing element. In some instances the joint is a pivoting joint. In other instances the joint is a compressible joint.

In some instances, the intervertebral stabilization system will include only a single stabilizing element disposed longitudinally on one side of the spinous processes. However, in other embodiments, the intervertebral stabilization system desirably includes two stabilizing elements disposed longitudinally in a substantially parallel relationship on opposite sides of the spinal processes. In this latter embodiment, the two stabilizing elements may be connected by a transverse connecting rod that desirably, but not necessarily, includes a pivoting joint.

The stabilizing element is used in conjunction with a disc prosthesis or a disc nucleus replacement disposed between adjacent vertebra in a spinal column. The disc prosthesis may be any suitable prosthesis capable of retaining or simulating at least one natural intervertebral motion. The disc prosthesis that is used in conjunction with the stabilizing elements may have a variety of designs, many of which have been proposed in the literature. Suitable disc prostheses include, but are not limited to, those that include a ball-in-socket mechanism, those that include a mechanical damping mechanism, and those that include a flexible or elastomeric polymer insert.

In one embodiment, a spinal stabilization system includes a stabilizing element comprising a first segment and a second segment connected by a pivoting joint. The first segment is attached to a first vertebra by a first connector and the second segment is attached to a second vertebra by a second connector, such that the stabilizing element adopts a substantially parallel alignment with respect to the longitudinal axis of the spinal column. The pivoting joint may take on a variety of forms, provided it allows the stabilizing element to undergo a bending or flexion/extension motion at the joint. In one exemplary embodiment, the stabilizing element is composed of two segments, wherein a proximal end of the first segment defines a ball and a proximal end of the second segment defines a complimentary spherical socket. In this construction, the ball and socket fit together to provide a pivoting joint.

In another exemplary embodiment, the stabilizing element is composed of two segments, wherein a socket defined by two opposing concave surfaces separated by a gap extends into the proximal end of the first segment. An insert characterized by two opposing convex surfaces extends outwardly from the proximal end of the second segment. The insert is adapted to fit into the socket to provide a pivoting joint based on a ball-and-socket type mechanism.

Another aspect of the invention provides a spinal stabilization system that includes at least one dynamic stabilizing element in combination with a disc prosthesis. As used herein, a "dynamic" stabilizing element is an element that allows for at least one natural intervertebral motion when it is disposed along a spinal column. Like the jointed stabilizing elements provided herein, the dynamic stabilizing elements may be used to stabilize the spinal column while preserving or accommodating at least some of the natural motions of a facet joint after a prior destabilizing procedure, such as a facetectomy. Unlike the jointed stabilizing elements, these dynamic stabilizing elements do not require a joint to provide motion. Suitable dynamic stabilizing elements have been proposed for correcting spinal deformities, such as those related to scoliosis, or for relieving pressure on a damaged disc. However, it has not been recognized previously that such dynamic stabilizing elements may advantageously be used in combination with one or more disc prostheses or disc nucleus replacements in order to stabilize a spine without partially or wholly sacrificing natural intervertebral and facet joint motion.

Like the jointed stabilizing elements, the dynamic stabilizing elements will typically be located at the posterior of the spine, but other placements, including lateral and anterior placements, are possible. The dynamic stabilizing elements may further be attached to various areas of the vertebrae including the main body of the vertebrae, the spinous process and the facet joint, and may be implanted by an open procedure, endoscopically or laproscopically.

In one embodiment of this aspect of the invention, the dynamic stabilizing element includes a curved rod attached to a first vertebra by a first connector and to a second vertebra by a second connector. The connectors are coupled to the curved rod in a manner that allows for translation of the rod along the axis of curvature of the spine. The dynamic stabilizing element further may include a damping element, such as a spring, working in conjunction with the dynamic stabilizing element to damp axial loading, or to restrict the motion of the rod. between the vertebrae.

In some embodiments of this aspect of the invention, the spinal stabilization system includes two or more dynamic stabilizing elements in combination with the disc prosthesis. Here, each dynamic stabilizing element includes a damping element, such as a spring, connected between a first and second vertebra by a first connector and a second connector. The connectors may include pedicle screws, lateral mass screws, hooks, polyaxial pedicle screws, polyaxial hooks, or the like.

BRIEF DESCRIPTION OF THE DRAWINGS

FIG. 3 shows a posterior cross-sectional view of the two segments in FIG. 2 connected to form a pivoting joint.

FIG. 4 shows a posterior view of the stabilizing element of FIG. 3.

FIG. 5 shows a lateral cross-sectional view of the stabilizing element of FIG. 3.

FIG. 6 shows a stabilizing element having a tilted pivoting joint.

FIG. 13 shows a cross-sectional posterior view of the stabilizing element wherein the two segments that connect to form a pivoting joint are each composed of multiple sections.

FIG. 14 shows a stabilizing element composed of two segments connected together by a compressible joint, wherein the stabilizing element is a stabilizing rod.

DETAILED DESCRIPTION OF THE PREFERRED EMBODIMENTS

Figure 1:
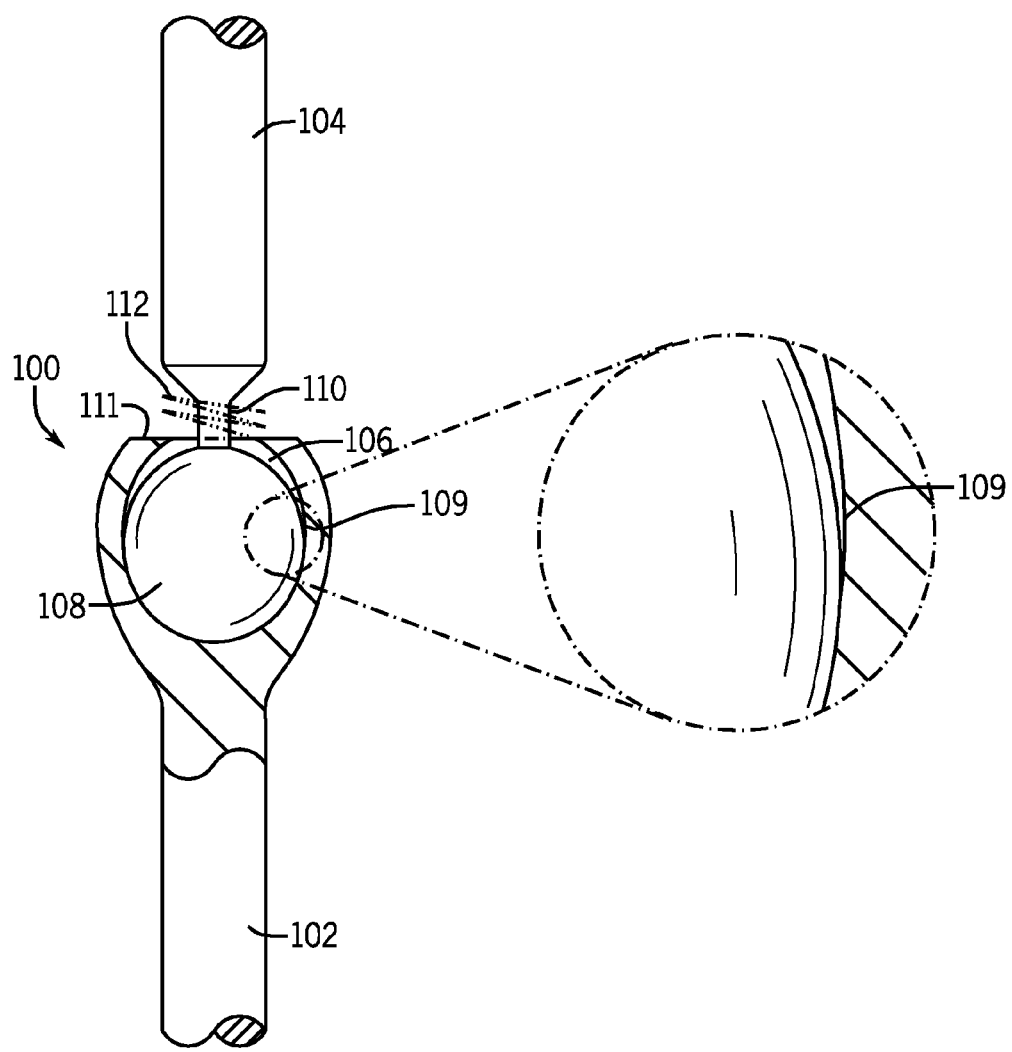
FIG. 1 shows a cross-sectional view of a stabilizing element having a ball-and-socket type joint.

Non-rigid spinal stabilizing elements and spinal stabilization systems which combine the spinal stabilizing elements with disc prostheses or disc nucleus replacements are provided herein. The spinal stabilization systems are designed to retain or simulate at least some of the physiological intervertebral mobility of the spine by distributing the stress and mobility functions between one or more disc prostheses or disc nucleus replacements and one or more stabilizing elements. The stabilizing elements and stabilization systems provided herein are useful for stabilizing the cervical, thoracic and lumbar regions of the spine, may be combined with one or more prosthetic vertebral bodies and may be used to preserve the natural mobility of a facet joint in patients with facet disease or patients who have had a prior destabilizing procedure, such as a facetectomy or a laminectomy.

A first aspect of the invention provides a spinal stabilization system that includes the following basic elements: 1) a segmented stabilizing element composed of at least two segments; 2) a joint connecting the at least two segments of the stabilizing element; 3) a first connector adapted to connect the stabilizing element with a first vertebra in a spinal column; 4) a second connector adapted to connect the stabilizing element to a second vertebra in the spinal column; and 5) a disc prosthesis or disc nucleus replacement adapted to be inserted into an intervertebral space between two adjacent vertebra in the spinal column. Each of these basic elements will be described in more detail below.

The stabilizing elements of the spinal stabilization system are designed to stabilize the spine by relieving some of the stress on an intervertebral disc prosthesis and to preserve at least some of the natural motion of one or more facet joints. The stabilizing elements are a trans-vertebral stabilizing element. As such, the stabilizing elements span two or more vertebra in the spine and are located outside of the intervertebral spaces in the spinal column. The stabilizing elements will typically be located at the posterior of the spine, but other placements including lateral and anterior placements are also possible. The stabilizing elements may be implanted by an open procedure, endoscopically or laprascopically. The spinal stabilization systems may include a single stabilizing element or two or more stabilizing elements. When only a single stabilizing element is included, that stabilizing element is generally disposed posteriorly to one side of the spinous processes. When two stabilizing elements are included in the system, they are typically disposed in a spaced apart, substantially parallel arrangement wherein one of the stabilizing elements is placed on either side of the spinous processes. In spinal stabilization systems that include two or more stabilizing elements, the elements optionally may be connected together through a transverse connector. Like the stabilizing elements, the transverse connectors may be composed of two or more segments connected together by a joint, typically a pivoting joint.

The stabilizing elements are typically rods or plates having a long dimension that runs along the long dimension of the spine when the stabilizing element is implanted in a patient. Spinal stabilizing rods and plates have been described in the literature. These include, but are not limited to, the rods described in U.S. Pat. Nos. 6,554,831 and 4,743,260, the disclosures of which are incorporated herein by reference. Also included are the plates described in published U.S. Patent Application No. 2001/0037111 and U.S. Pat. No. 5,352,224, the disclosures of which are incorporated herein by reference. These rods and plates may be adapted for use as stabilizing elements in the present invention by inserting one or more connecting joints along their lengths.

Each segment of the stabilizing element may be composed of a single integrally formed unit. Alternatively, one or more of the segments may be sectional, that is, composed of a plurality of interlocking sections. For example, the segments of a stabilizing rod may be divided into sections that screw together end to end. This design allows the length of a segment to be tailored to fit a particular patient or a particular placement of the stabilizing elements along a spine. In addition, this design makes it possible to easily switch out the sections that form the joint for rigid sections. This may be a desirable option, for example, when a disc prosthesis is exchanged for or converted into a fusion. Additionally, the segments may be adapted to be inserted into pre-existing stabilizing devices.

The at least two segments of the stabilizing element are connected by a joint. In this configuration, the joint serves at least two purposes. First, the joint serves to fasten the two segments of the stabilizing element together, and second, the joint provides for at least one degree of motion between the two segments. For example, the joint may be designed to provide or accommodate spinal flexion and extension and/or a lateral bending motion. For the purpose of this disclosure, a joint that provides or accommodates a flexion and extension and/or a lateral bending motion is referred to as a pivoting joint. Alternatively, the joint may provide, accommodate, or damp spinal compression/expansion type motion. For the purposes of this disclosure, a joint that provides, accommodates, or damps a spinal compression/expansion motion is referred to as a compressible joint. In some embodiments, the joint may provide or accommodate a combination of the above-mentioned motions. In some instances, it is desirable to provide restrictive elements that restrict the extent of motion provided by the joint in order to more accurately simulate the natural motion of the spine.

Suitable pivoting joints include ball-and-socket type joints and joints based on a ball-and-socket type mechanism (i.e., joints including complimentary concave and convex surfaces). Spinal stabilizing elements including pivoting joints for use in combination with bone fusions have been proposed. These spinal stabilizing elements may be used in combination with one or more intervertebral disc prostheses or one or more disc nucleus replacements to provide a spinal stabilization system in accordance with the present invention. A jointed intervertebral link device that may be used as a stabilizing element in the spinal stabilization systems provided herein is described in U.S. Pat. No. 6,241,730, the entire disclosure of which is incorporated herein by reference. Briefly, the pivoting joint of the '730 patent includes a socket extending into the proximal end of a first segment and a pin extending outwardly from the proximal end of a second segment, the pin having a distal end and an outwardly extending radial collar. A first damping element is disposed around the pin above the collar and a second damping element is disposed around the pin below the collar. The pin and the first and second damping elements extend into the socket to form a joint that allows for multidirectional pivoting of the pin in the socket.

Another suitable ball-and-socket joint design is described in reference to a jointed cross-link for an implantable spinal apparatus in U.S. Pat. No. 6,554,831 (see, e.g., FIG. 4), the entire disclosure of which is incorporated herein by reference. This joint is based on a ball-and-socket mechanism wherein a first segment has a proximal end defining a socket for receiving a ball integrally formed at the proximal end of a second segment. Together, the ball-and-socket provide a pivoting joint that connects the two segments. This type of joint may be used as a pivoting joint in a transverse connector. Other illustrative joint designs are shown in FIGS. 2-13, discussed in greater detail below.

Connectors are used to attach the stabilizing elements along the spinal column. The connectors may include any suitable connecting means capable of securing a stabilizing element to a vertebra. Suitable connectors include, but are not limited to, pedicle screws, hooks, and lateral mass screws. The connectors will typically include a shaft, such as a rod, hook, nail or threaded screw shaft, that is adapted to penetrate or anchor to a bone and a securing portion adapted to secure the stabilizing element. For example, the connector may be a bone screw having a coarse thread on one end for threading into a bone and a machine thread on the opposing end for screwing into a matching tapped bore in a stabilizing element. The connector may itself include multiple elements. For example, the connector may include a screw or hook secured to a rod clamp for connecting a stabilizing rod to a bone.

In some embodiments, the connectors include polyaxial screws or hooks. Such screws or hooks allow for the accommodation of differing orientations and positioning between screws implanted in a series and may provide one or more degrees of motion between the connectors and the stabilizing elements to which they are attached. Suitable polyaxial pedicle screws and hooks for use as connectors in the spinal stabilization systems provided herein are disclosed in U.S. Pat. Nos. 5,591,166, 5,628,740, and 6,626,908 the entire disclosures of which are incorporated herein by reference. In order to provide for an articulating connection, the polyaxial pedicle screws disclosed in U.S. Pat. Nos. 5,591,166 and 5,628,740, may be used without being locked into a fixed orientation such that the stabilizing elements retain a relative motion with respect to the shaft of the connector.

The connectors desirably, but not necessarily, provide a rotatably adjustable connection to the stabilizing elements. As used herein, a rotatably adjustable connection refers to a connection that allows the stabilizing elements, or individual segments thereof, to be rotated about their longitudinal axes before, during or after implantation of the spinal stabilization systems in order to allow the surgeon to optimize the orientation of the joint relative to the patient's spine. The connectors may include a locking mechanism adapted to lock-in the orientation, preventing further rotation once the orientation of the stabilizing element has been optimized. The pedicle screws described in U.S. Pat. Nos. 5,591,166 and 5,628,740, would be capable of serving this function. In one such embodiment, the stabilizing element is a rod and the connector is a screw including a threaded shaft and a head having a lateral (i.e., perpendicular to the long axis of the shaft) bore extending therethrough. The diameter of the rod is small enough to allow the rod to pass through the bore and rotate therein. Once the rotational orientation of the rod has been optimized, a set screw, or other locking mechanism, is provided to clamp down on, or screw into, the rod, fixing its rotational orientation.

The connectors may be used to connect the stabilizing elements to adjacent or non-adjacent vertebrae in a spinal column. The connectors are desirably, but not necessarily, attached to same vertebrae between which the disc prosthesis or disc nucleus replacement is disposed or to a prosthetic vertebral body or bodies. In some instances, the connectors may be associated with pre-existing stabilizing devices, such that the stabilizing elements provided herein may be incorporated into or replace components of such devices.

In the spinal stabilization systems, the stabilizing elements are used in conjunction with at least one disc prosthesis or at least one disc nucleus replacement. In these systems, the prosthesis or replacement is contained within an intervertebral space that is spanned by one or more stabilizing elements. A variety of intervertebral disc prostheses may be used in conjunction with the spinal stabilization elements provided herein. Many such disc prostheses have been proposed. For example, the disc prosthesis may include a mechanical damping element, such as a spring, disposed between an inferior base plate adapted to be attached to an inferior vertebra, and a superior base plate adapted to be attached to a superior vertebra. Alternatively, the disc prosthesis may include a rubber, gel, or polymeric insert disposed between an inferior and a superior base plate. The disc prosthesis may be based on a ball-and-socket mechanism wherein one or more pairs of complementary concave and convex surfaces come together to form a joint. Suitable disc prostheses that may be used in the spinal stabilization systems provided herein include, but are not limited to, those described in U.S. Pat. Nos. 5,556, 431; 5,401,269; 5,314,477; 6,368,350; 6,146,421; 6,139,579; and 5,562,738, the entire disclosures of which are incorporated herein by reference. Other suitable disc prostheses are described in U.S. patent application Ser. No. 10/675,573, filed Sep. 30, 2003, the entire disclosure of which is incorporated herein by reference. The stabilizing elements may also be used with an artificial disc nucleus, such as a hydrogel-based nucleus replacement.

The spinal stabilizing elements and spinal stabilization systems provided herein may span a single intervertebral space between two adjacent vertebra, or may span multiple intervertebral spaces, and possibly multiple disc prostheses and/or disc nucleus replacements, along a patient's spine.

The spinal stabilization systems provided herein may also optionally include one or more prosthetic vertebral bodies spanned by one or more stabilizing elements. Suitable prosthetic vertebral bodies for incorporation into the spinal stabilization systems provided herein have been described in the literature. These include, but are not limited to, the prosthetic vertebral bodies described in U.S. Pat. Nos. 4,932,975; 5,306, 310; 5,147,404; 5,989,290; and 6,001,130, the entire disclosures of which are incorporated herein by reference. Another suitable vertebral prosthesis that may be used with the spinal stabilization systems provided herein is described in U.S. patent application Ser. No. 10/675,573, filed Sep. 30, 2003. In embodiments where a prosthetic vertebral body is included, the connectors may connect the stabilizing elements to the prosthetic vertebral body or to a vertebra. Thus, as used herein, the phrases "connected to a vertebra" or "adapted to be connected to a vertebra" refer to connections to natural and artificial vertebrae.

Figure 11:
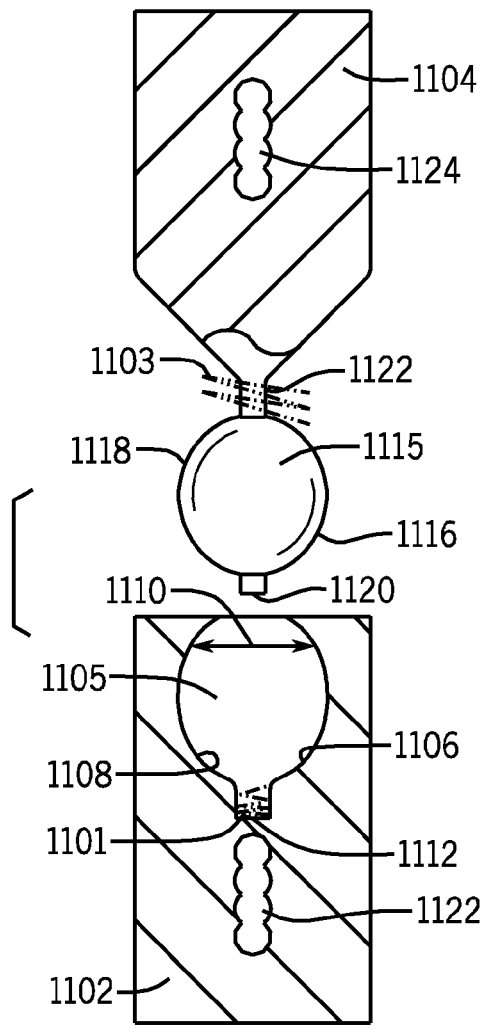
FIG. 11 shows a cross-sectional posterior view of the two segments of the stabilizing element that come together to form a pivoting joint, wherein the stabilizing element is a stabilizing plate.
Figure 12:
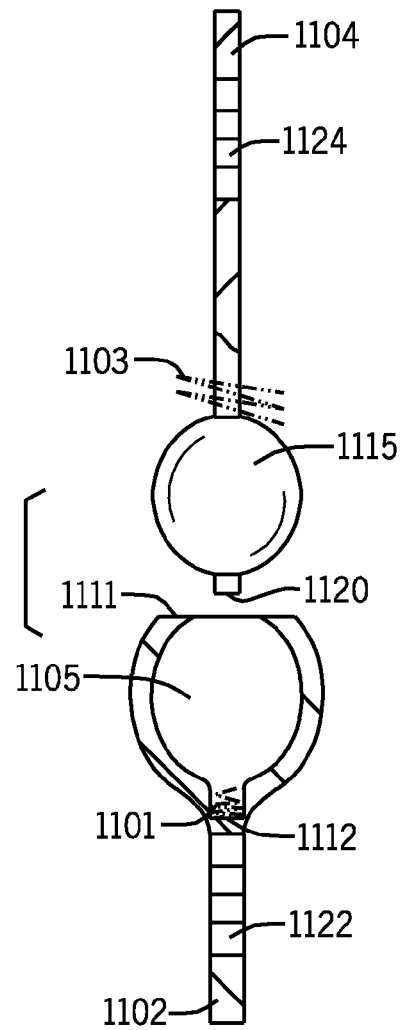
FIG. 12 shows a lateral cross-sectional view of the stabilizing element of FIG. 11.

FIGS. 1-13 show examples of pivoting joints that may be used to connect the first and second segments of a stabilizing element in the spinal stabilization systems provided herein. In FIGS. 1-10 and 13, a rod is used as an illustrative stabilizing element. In FIGS. 11 and 12, a plate is used as an illustrative stabilizing element.

In the description of these figures, and throughout the specification, the terms "longitudinal" and "proximal" are used as relative terms. The term "longitudinal" is used to refer to the direction running lengthwise along the long dimension of a stabilizing element. The term "proximal" is used to refer to the location nearer to a joint.

The embodiments shown in the figures are intended only to exemplify the invention and should not be construed to limit the invention to any particular embodiment. The drawings are not necessarily to scale and the relative dimensions of the components of the stabilizing elements and the stabilization systems provided therein may deviate from those shown in the figures.

FIG. 1 shows a ball-and-socket type joint 100. The joint depicted in FIG. 1 includes a first segment 102 having a generally spherical socket 106 extending into the proximal end thereof. The stabilizing element 100 further includes a second segment 104 having a ball 108 disposed on the proximal end thereof. The second segment 104 and the ball 108 are desirably, but not necessarily, integrally formed as one piece separated by a neck 110. As shown in FIG. 1, the ball 108 and socket 106 fit together to provide a rotating joint.

When this joint is connected, the sidewalls of the spherical socket should extend upwardly beyond the maximum diameter of the ball in order to prevent the ball from becoming dislodged from the socket. As best seen in the blown-up section of FIG. 1, the socket is desirably characterized by a flat strip 109 extending laterally around its midsection in order to allow for translation in the longitudinal direction. The second segment 104 may optionally include a spring disposed around its neck in order to provide damping or restriction of translational, flexion, extension or lateral bending motions. The pivoting joint may be formed by press fitting the ball into the socket. Alternatively, diametrically opposed longitudinal slits (not shown) may be formed in the walls of the socket to provide the socket with a certain degree of flexibility, thus enabling the ball to slide more easily into the socket. In the embodiment shown in FIG. 1, the neck 110 of the second segment 104 provides a certain amount of clearance between the first and second segments of the stabilizing element. The amount of clearance provided by the neck 110 can influence how far the two segments may pivot before coming into abutment and preventing further pivoting motion. The clearance provided by the neck 110 need not be uniform on all sides of the stabilizing element 100. For example, the shape of the circumference of the neck 110 or the shape of the upper surface 111 of the second segment 102 may be designed to allow pivoting in some directions, but not in others. Thus, the stabilizing element may be designed to accommodate flexion and extension to a certain degree and lateral bending to a lesser degree.

Figure 2:
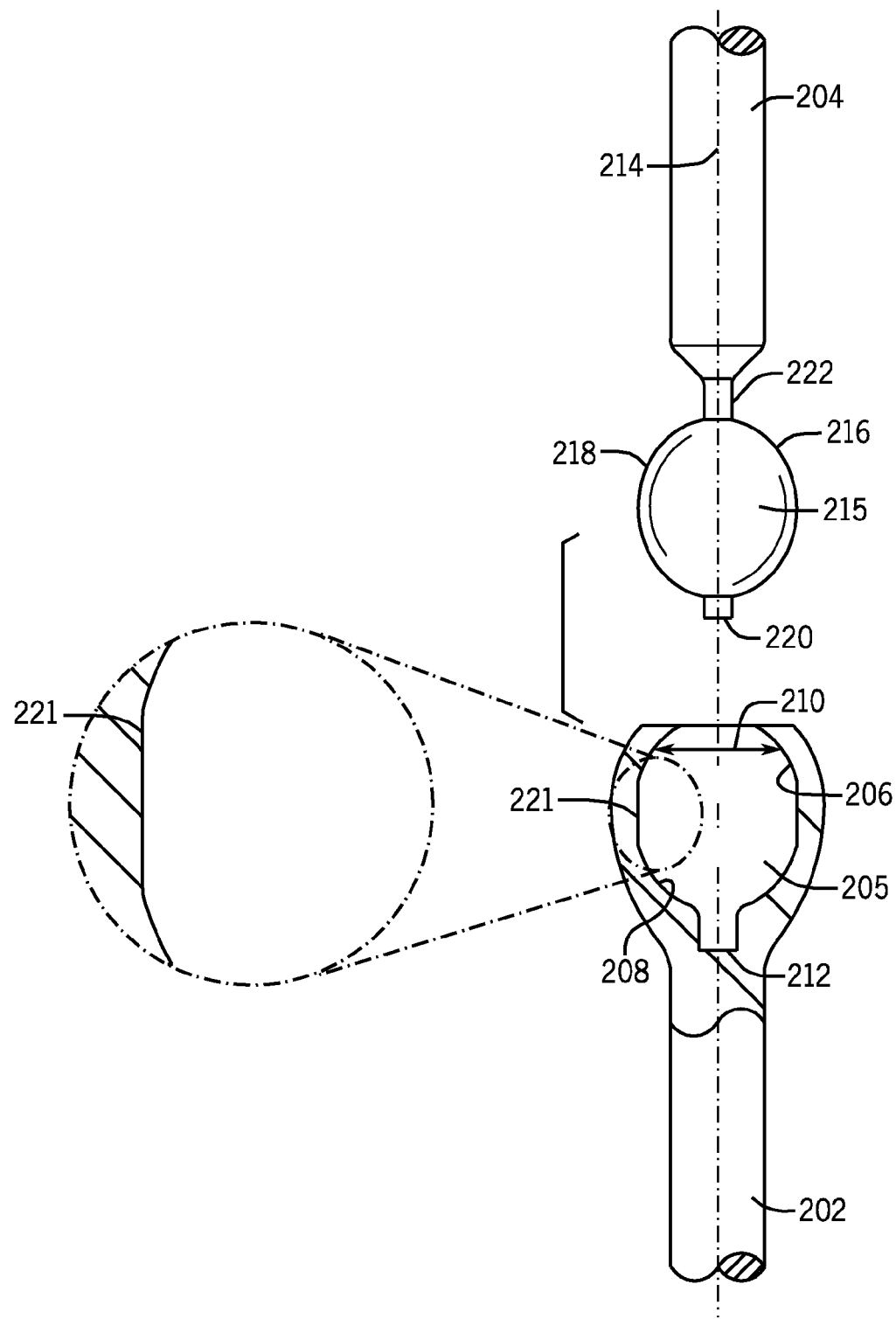
FIG. 2 shows a cross-sectional posterior view of the two segments of a stabilizing element that come together to form a pivoting joint, wherein the stabilizing element is a stabilizing rod.

FIGS. 2-6 depict an alternative embodiment of a pivoting joint that may be used to connect the two segments of the stabilizing element in a spinal stabilization system. FIG. 3 shows a cross-sectional front view of the stabilizing element. It should be understood that the "front" view may correspond to an anterior, lateral or posterior view, depending on the intended orientation of the stabilizing element in the patent's spine. For purposes of illustration only, the front view in FIG. 3 may be considered to be a posterior view, such that the plane extending perpendicularly into plane of the figure and bisecting the stabilizing element may be referred to as the "sagittal" plane and the plane lying in the plane of the figure and bisecting the stabilizing element may be referred to as the "lateral" plane. In this embodiment, the stabilizing element includes a first segment 202 having a socket 205 extending into the proximal end thereof. This socket 205 is defined by two opposing concave surfaces 206, 208 separated by a gap 210. As best shown in the blown-up section of FIG. 2, the opposing concave surfaces desirably include a flat strip 221 running laterally through the apex of their concavity. The socket shown in FIG. 2 is further defined by a lower housing 212 centered on the longitudinal axis 214 of the stabilizing element and opening into the gap 210. The stabilizing element further includes a second segment 204 having an insert 215 disposed on its proximal end. The insert is characterized by two opposing convex surfaces 216, 218 and is desirably, but not necessarily, integrally formed on the proximal end of the second segment 204. As shown in the contrasting views of FIGS. 3 and 5, the insert is disc-shaped, that is, it is wider in one dimension than the other. This design is advantageous because it limits the rotation of the joint about its longitudinal axis 214. The outermost end of the insert 215 desirably includes a flat extension 220, while the opposing end forms a neck 222 in the second segment 204.

FIG. 3 shows a pivoting joint formed by fitting the insert 215 into the socket 205 to connect the first segment 202 and the second segment 204 of the stabilizing element. This design allows the joint to pivot to a greater degree in the sagittal plane than in the lateral plane. The extent to which the joint may pivot in the sagittal plane will be determined, at least in part, by the clearance between the upper surface 211 of the first segment 202 and the shaft 213 of the second segment 204 provided by the neck 222 in the second segment. As shown in FIG. 4, the extent to which the joint may pivot may be increased by cutting a groove 400 into the proximal end of the first segment 202. The flat extension 220 on the outmost end of the socket 205 may extend into the socket housing 212 in order to accommodate longitudinal translation of one segment with respect to the other. Optionally, a spring 300 may be inserted into the housing 212 of the socket 215 in order to damp axial loading on the joint. A side view of the stabilizing element of FIG. 3 is shown in FIG. 5.

The sockets extending into the proximal ends of the segments may be characterized by a central axis, which is the axis running through the center of the opening of the socket at the outermost end of the segment. In the embodiment depicted in FIGS. 2-5, the pivoting joint pivots about a central axis that coincides with a longitudinal axis 214 of the stabilizing element. However, in some applications, it may be desirable for the pivoting joint to pivot about a central axis that is not coincident with the longitudinal axis of the stabilizing element. Such an embodiment is depicted in FIG. 6. In this embodiment, the stabilizing element 600 includes a first segment 602 having a socket extending into its proximal end. This socket is defined in part by two opposing concave surfaces 606, 608 separated by a gap. The stabilizing element 600 further includes a second segment 604 having an insert 615 disposed on its proximal end. The insert is characterized by two opposing convex surfaces 616, 618. Unlike the joints shown in FIGS. 2-5, the joint shown in FIG. 6 pivots about a central axis 622 that is not coincident with or parallel to the longitudinal axis 626 of the stabilizing element. Rather, the joint of FIG. 6 pivots about an axis 622 that forms an angle 624 with the longitudinal axis 626 of the stabilizing element. This design is advantageous because it allows a surgeon to optimize the orientation of the joint relative to the spinal column by rotating the first and second segments of the stabilizing element. In this manner, the pivoting joint may be properly aligned with the natural facet plane of each individual patient.

Figure 7:
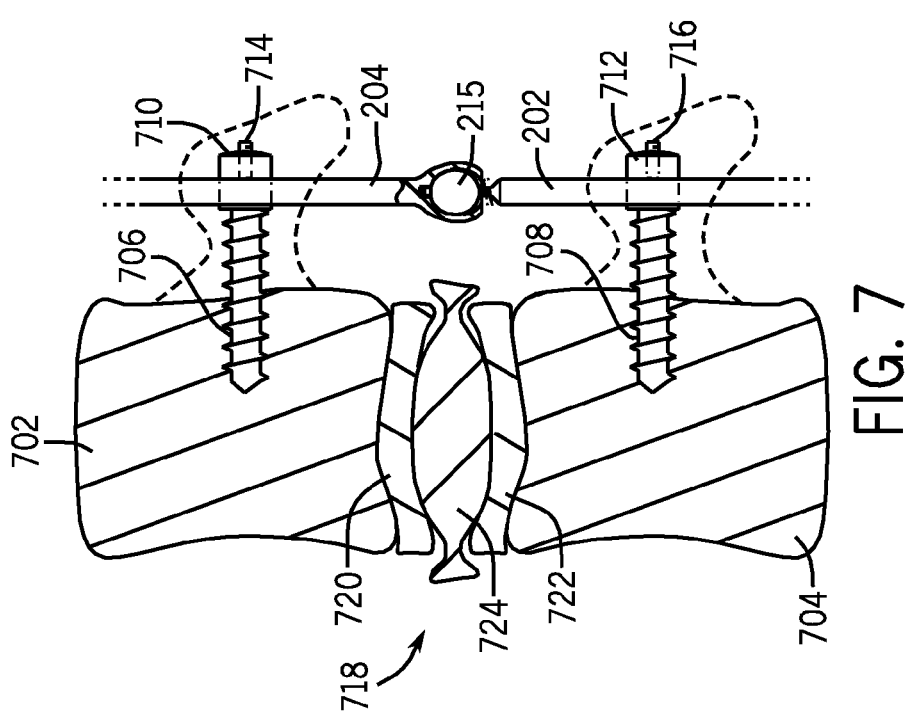
FIG. 7 shows a stabilization system implanted in a spine, including the stabilizing element of FIGS. 2-5 and a disc prosthesis.

FIG. 7 shows a cross-sectional, lateral view of a spinal stabilization system that includes the spinal stabilizing element of FIGS. 2-5 in combination with an intervertebral disc prosthesis. The spinal stabilizing element is connected across a first vertebra 702 and a second vertebra 704 to one side of the spinal processes (shown in dotted lines) at the posterior of the spine. In the exemplary embodiment shown in FIG. 7, the stabilizing element is connected to the vertebrae using pedicle screws 706, 708. The pedicle screws each include a screw head 710, 712 having a lateral bore extending therethrough. The first and second segments of the stabilizing element extend through the lateral bores in the first and second pedicle screw heads respectively. As shown in the figures, the first and second segments may be fixed to the pedicle screws by set screws 714, 716 that screw through the screw heads 710, 712 and press against or screw into or through the first and second segments of the stabilizing element. Of course, many other connectors and connector configurations may be used to attach the segments to the vertebrae.

The intervertebral disc prosthesis of the spinal stabilization system of FIG. 7 includes an inferior base plate 722 adapted to be connected to the inferior vertebra 704 and a superior base plate 720 adapted to be connected to the superior vertebra 702. The inferior base plate is characterized by an upwardly-facing concave surface which faces an oppositely disposed concave surface of the superior base plate 720. The disc prosthesis further includes a disc insert 724 sandwiched between the superior and inferior base plates 720, 722. The disc insert 724 is characterized by two opposing convex surfaces which complement the concave surfaces of the superior and inferior base plates 720, 722 in order to provide one or more degrees of motion between the superior and inferior vertebrae 702, 704. A more detailed description of the disc insert is provided in U.S. patent application Ser. No. 10/675,573.

Figure 8:
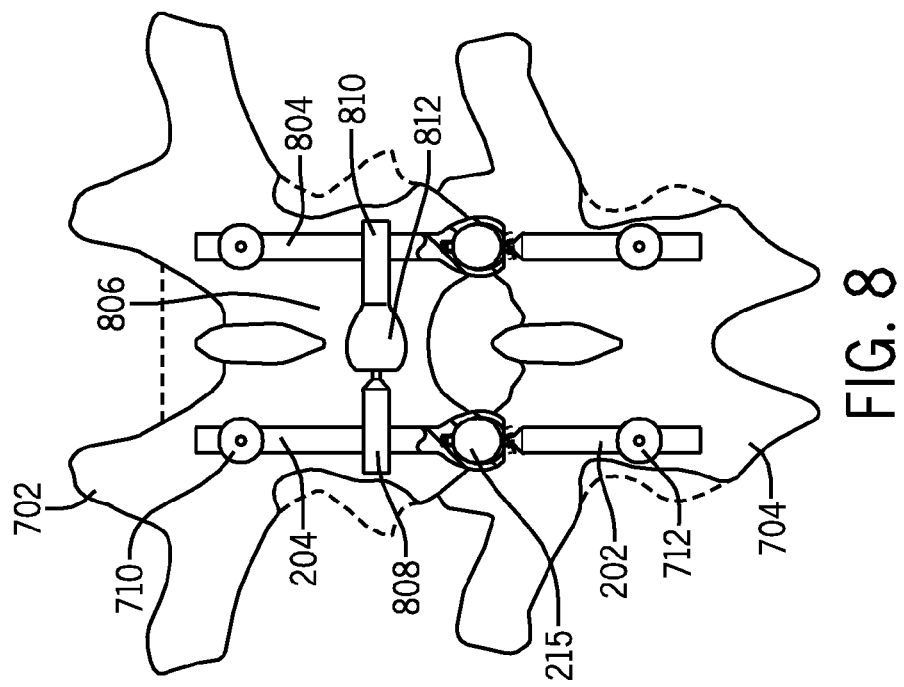
FIG. 8 shows a posterior view of a spinal stabilization system implanted in a spine, including two stabilizing elements of the type shown in FIGS. 2-5 and an articulating transverse connector.

FIG. 8 shows a posterior view of the spinal stabilization system of FIG. 7. As shown in this figure, the spinal stabilization system includes two spinal stabilization elements disposed on opposite sides of the spinous processes. In the embodiment depicted in FIG. 8, the second segment 204 of the first stabilizing element and the second segment 804 of the second stabilizing element are connected by a transverse connector 806 which limits the ability of the two stabilizing elements to move independently with respect to each other. As shown in the figure, the transverse connector may itself include a first and a second segment 808, 810 connected by a joint 812, such as the ball-and-socket type joint shown in FIG. 1.

Figure 10:
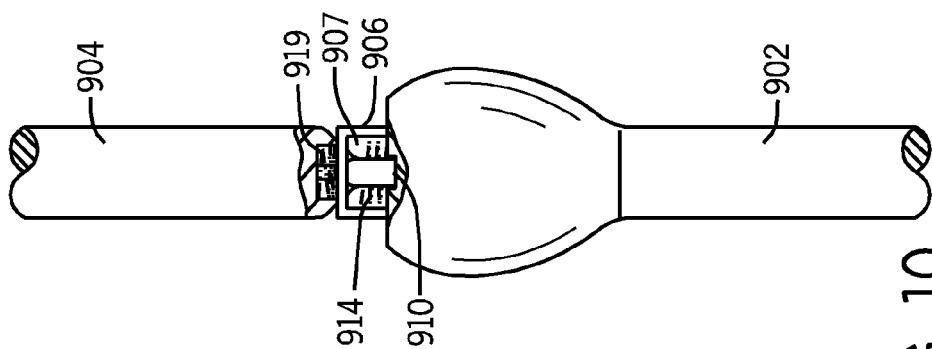
FIG. 10 shows a posterior view of the stabilizing element of FIG. 9.
Figure 9:
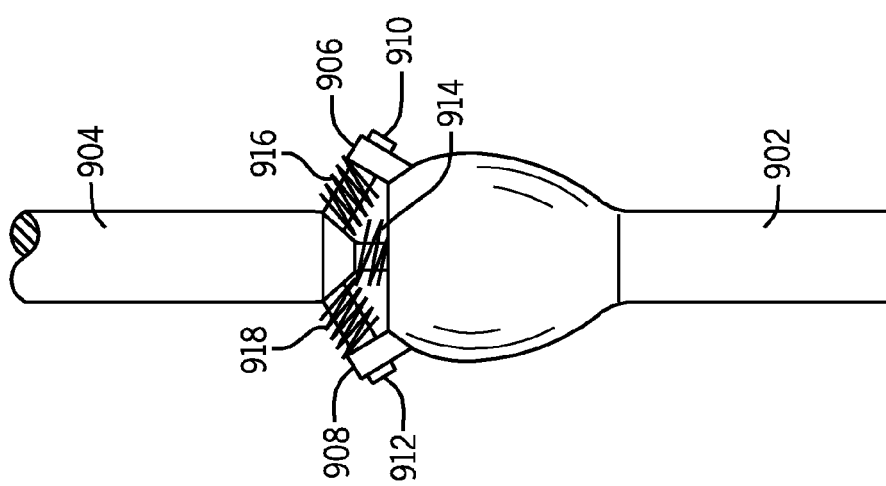
FIG. 9 shows a lateral view of a stabilizing element having damped flexion, extension, and translational motions.

FIGS. 9 and 10 show an alternative embodiment for a stabilizing element. As shown in the figures, the stabilizing element includes a first segment 902 having one or more tabs 906, 908 extending upwardly and outwardly from its proximal end. Each of the tabs defines an internal window 907. Although not explicitly shown in these figures, the first segment also includes a socket of the type shown in FIG. 2 extending into its proximal end. The stabilizing element further includes a second segment 904 having one or more arms 910, 912 extending downwardly and outwardly from its proximal end. Although not explicitly shown in the figures, the second segment also includes an insert of the type shown in FIG. 2 disposed on its proximal end. When the first and second segments 902, 904 are connected to form a joint, the arms 910, 912 of the second segment fit through the windows 907 in the tabs 906, 908 of the first segment 902. A first spring 914 is disposed around the neck of the second segment to provide for damping of axial loading on the joint. A second and a third spring 916, 918 are disposed around the arms 910, 912 of the second segment 904 in order to provide a damping or restriction of the flexion and extension or lateral motions of the joint. As best seen in FIG. 10, the dimensions of the window 907 is desirably greater than the dimensions of the arm 910 to allow for a certain degree of translation and rotation of the arm 910 within the window 907.

FIGS. 11 and 12 depict an embodiment of a pivoting joint that may be used to connect two segments of the stabilizing element in a spinal stabilization system, wherein the stabilizing element is a stabilizing plate. FIG. 11 shows a cross-sectional front view of the stabilizing element. In this embodiment, the plate includes a first segment 1102 having a socket 1105 extending into the proximal end thereof. As best shown in FIG. 12, the proximal end of the plate is expanded in order to accommodate the socket 1105. This socket 1105 is defined by two opposing concave surfaces 1106, 1108 separated by a gap 1110. The socket is further defined by a lower housing 1112 centered on the longitudinal axis of the stabilizing plate and opening into the gap 1110. The stabilizing plate further includes a second segment 1104 having an insert 1115 on its proximal end. The insert is characterized by two opposing convex surfaces 1116, 1118 and is desirably, but not necessarily, integrally formed on the proximal end of the second segment 1104. As shown in the contrasting views of FIGS. 11 and 12, the insert is disc-shaped, that is, it is wider in one dimension than the other. This design is advantageous because it limits the rotation of the joint about its longitudinal axis. The outermost end of the insert 1115 desirably includes a flat extension 1120 while the opposing end forms a neck 1122 in the second segment 1104. The opposing concave surfaces 1106, 1108 of the first segment 1102 desirably include a flat strip running laterally through the apex of their concavity. This flat strip allows a certain degree of longitudinal translation between the socket and the insert when the joint is connected. As shown in FIGS. 11 and 12, the two segments 1102, 1104 of the stabilizing element depicted therein each also include a slot 1122, 1124 extending through that segment. These slots are adapted to accept connectors, such as bone screws, hooks or nails in order to attach the stabilizing element to a vertebra.

FIG. 13 shows an embodiment of the stabilizing element of FIG. 3 wherein each of the first and second segments 202, 204 is composed of a plurality of interconnecting sections 1326, 1327, 1328, 1329, 1330. In the embodiment depicted in FIG. 13, the segments are connected end to end through a series of screw type connections 1332, 1333, 1334. As shown in the figure, one section 1326, 1328 of each segment 202, 204 includes a slot 1336, 1337 extending therethrough for accepting a connector such as a bone screw, hook or nail for attaching the stabilizing element to a vertebra. This embodiment makes it easy to adjust the length of the stabilizing element and to replace the joint sections 1327, 1330 with a rigid rod section in order to convert the pivoting stabilizing element into a rigid stabilizing element.

FIG. 14 shows a cross-sectional view of a portion of a stabilizing element that includes a compressible joint rather than a pivoting joint. In this embodiment, the stabilizing element includes a first segment 1402 and a second segment 1404. The first segment 1402 includes a piston 1406 extending outwardly from its proximal end. A housing 1408 is defined in the proximal end of the second segment 1404. When the two segments are connected to form a joint, the piston 1406 extends into the housing 1408 and a damping element 1410 is disposed between the distal end 1412 of the piston and the ceiling 1414 of the housing. The damping element depicted in FIG. 14 is a spring. However, any suitable damping element may be used provided that element is capable of damping the axial loading on the joint. Other suitable damping elements include polymer or gel-based elastomeric bumpers. The use of a damping element in the housing 1408 of the second segment 1404 eliminates the need for a damping fluid. This is advantageous because compressible joints that employ a damping fluid run the risk of leaking, causing an irritation, infection or toxicity in the patient.

Figure 15:
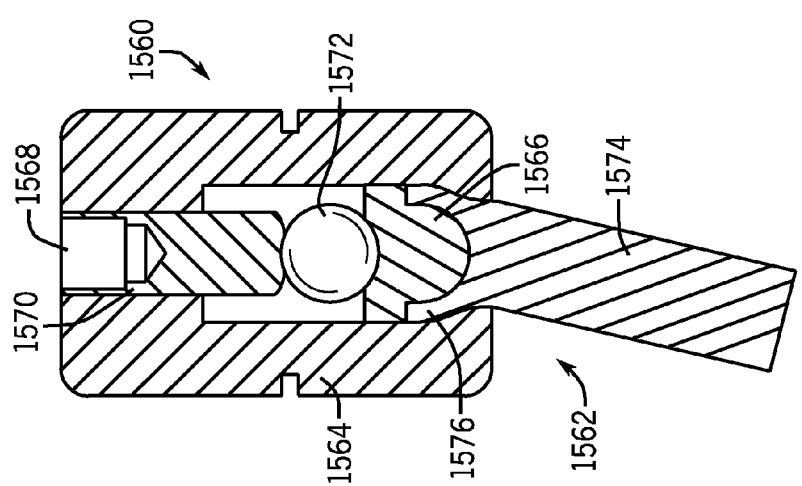
FIG. 15 shows a cross section of a polyaxial pedicle screw that may be used as a connector.

FIG. 15 shows an embodiment of a polyaxial pedicle screw 1560, of the type disclosed in U.S. Pat. No. 6,626,908, that may be used as a connector in the spinal stabilization systems provided herein. The polyaxial pedicle screw 1560 comprises a pedicle screw 1562, a housing 1564, a saddle shaped element 1566, a set screw 1568, a set screw aperture 1570, and a rod 1572. The pedicle screw comprises a screw stem 1574 and a screw head 1576. The housing 1564 has a through bore with a diameter at the top sufficient to allow the screw stem 1574 and the screw head 1576 of the pedicle screw 1562 through the housing. The through bore diameter narrows at the bottom of the housing 1564 sufficient to allow only the screw stem 1574 through the bottom of the housing 1564. The saddle shaped element 1566 extends across the width of the housing 1564 and can not be angularly displaced relative to the housing 1564. The saddle shaped element 1566 has a cylindrical shaped upper surface for engagement with the rod 1572. The saddle shaped element 1566 also has a spherical lower portion for engaging with the screw head 1576 that has a complementary spherical recess. The set screw 1568 is screwed into the set screw aperture 1570 to clamp the rod 1572 in position relative to the housing 1564. The engagement between the saddle shaped element 1566 and the screw head 1576 allows the housing 1564 to pivot with respect to the fixed pedicle screw 1562 thereby allowing the rod 1572 to pivot relative to the attachment point.

Figure 16:
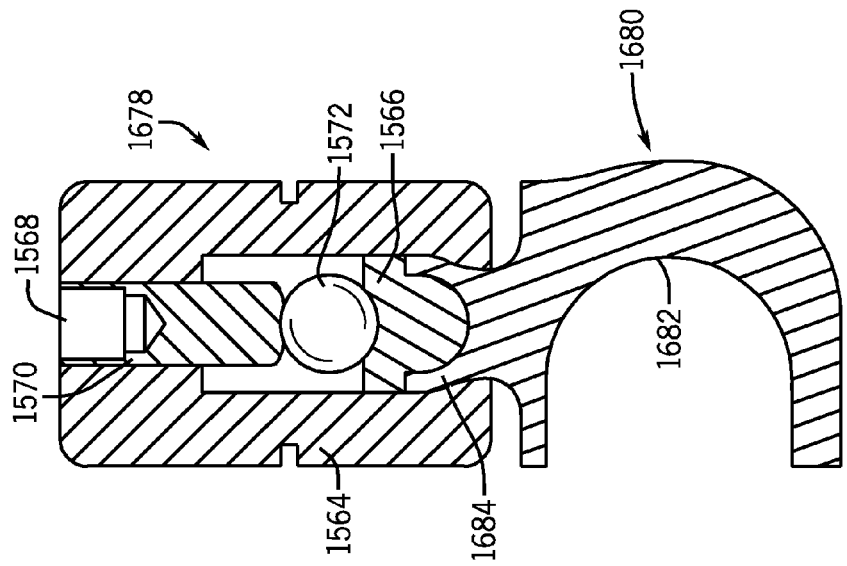
FIG. 16 shows a cross section of a polyaxial hook that may be used as a connector.

FIG. 16 shows a polyaxial hook 1678 that is similar to the polyaxial pedicle screw 1560 of FIG. 15 except that the pedicle screw 1562 has been replaced with a hook 1680 for attaching to the vertebra. The hook 1680 comprises a hook stem 1682 and a hook head 1684. The hook head 1684 similarly has a complementary spherical recess for engaging with the saddle shaped element 1566 and allowing the housing 1564 to pivot relative to the hook 1680.

A second aspect of the invention provides a spinal stabilization system that includes the following basic elements: 1) at least one dynamic stabilizing element; 2) a first connector adapted to connect the at least one dynamic stabilizing element to a first vertebrae in a spinal column; 3) a second connector adapted to connect the at least one dynamic stabilizing element to a second vertebra in the spinal column; and 4) a disc prosthesis or disc nucleus replacement adapted to be inserted into an intervertebral space between two adjacent vertebrae in the spinal column. Each of these basic elements will be described in more detail below.

Examples of suitable disc prostheses, disc nucleus replacements and connectors for use with the spinal stabilization systems of this aspect of the invention have been discussed previously in this disclosure. The connectors may attach the stabilizing elements to the same vertebra between which the disc prosthesis or disc nucleus replacement is disposed, or to other vertebra in the spinal column.

Figure 18:
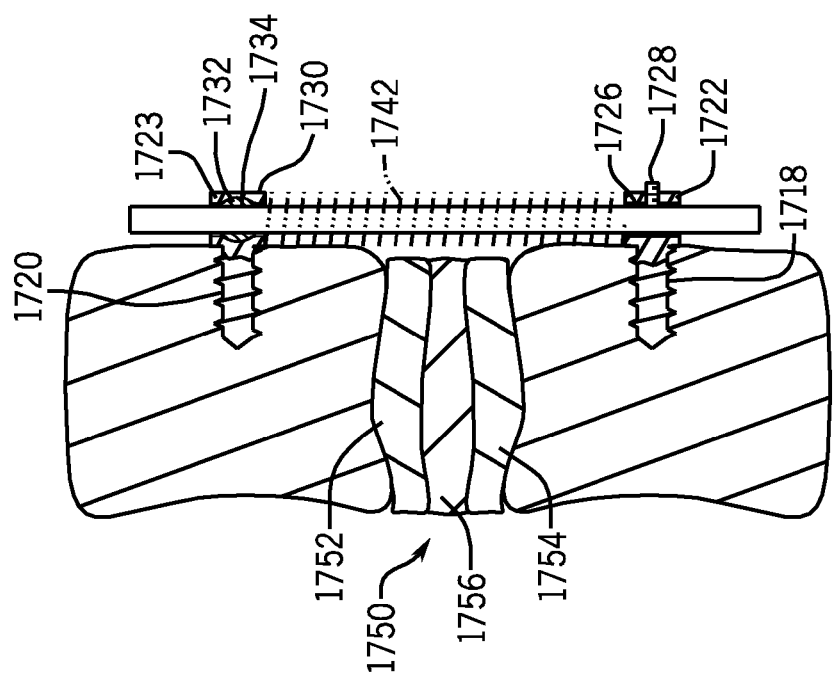
FIG. 18 shows a cross-sectional lateral view of the spinal stabilization system of FIG. 17, including a disc prosthesis.
Figure 17:
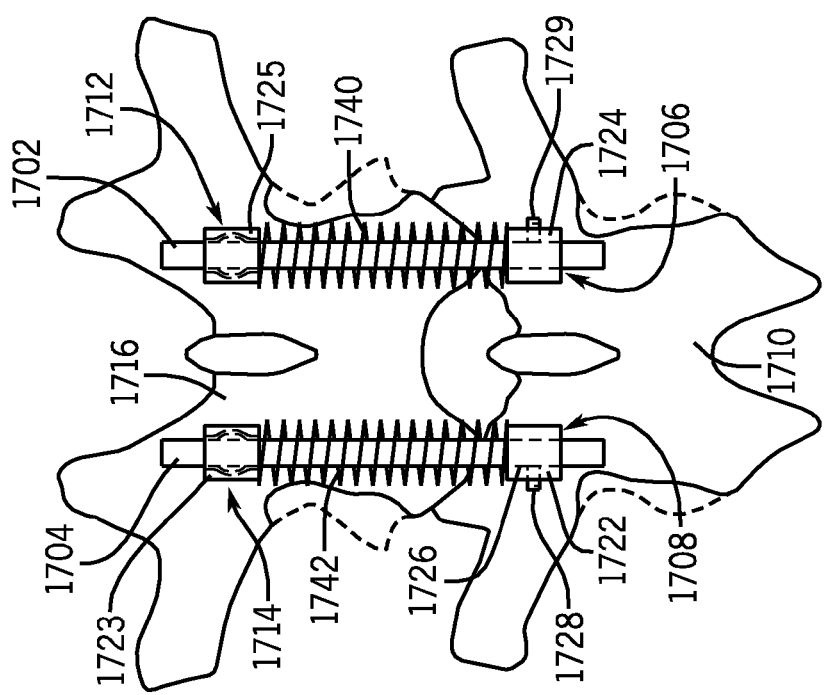
FIG. 17 shows a posterior view of a spinal stabilization system that includes two dynamic stabilizing elements.

In a first embodiment, in accordance with this aspect of the invention, the dynamic stabilizing element is the dynamic spinal orthosis disclosed in U.S. Pat. No. 5,672,175, the disclosure of which is incorporated herein by reference. FIGS. 17 and 18 illustrate a spinal stabilization system that used two spinal stabilizing elements similar to those disclosed in the '174 Patent. Here, the spinal stabilization system includes two dynamic stabilizing elements, each composed of a flexible rod 1702, 1704. The flexible rods are each attached to one vertebra in a manner that allows the rod to translate longitudinally with respect to that vertebra, where a "longitudinal" translation refers to a translation along the long axis of the spine. The flexible rods are also each attached to another vertebra in a manner that does not allow the rod to translate longitudinally with respect to that vertebra. In the embodiment depicted in FIG. 17, each rod is attached by a first connector 1706, 1708 to a first vertebra 1710 and by a second connector 1712, 1714 to a second vertebra 1716. Each connector includes a shaft 1718, 1720 (e.g., a nail, pin, hook or threaded screw shaft) that provides a connection to a bone or a prosthetic vertebral body and a securing portion 1722, 1723, 1724, 1725 that provides a connection to the flexible rod. The first connector 1706, 1708 is adapted to provide a rigid attachment to the flexible rod 1702, 1704, that is, an attachment that prevents relative motion between the flexible rod and the shaft of the connector. In one simple variation of this embodiment, the shaft 1718 of the first connector is a threaded screw shaft adapted to penetrate into a bone 1710 and the rod securing portion is a screw head 1722, 1724 (or nail head or hook head) having a bore 1726 extending therethrough. In this embodiment, the flexible rod 1702, 1704 is inserted through the bore 1726 and locked into a fixed position by one or more transverse set screws 1728, 1729 that screw against, into or through the rod 1702, 1704 after it has been inserted into the bore. In this embodiment, the shaft of the second connector may also be a threaded screw shaft 1720 (or nail shaft or hook) adapted to penetrate into a bone 1716 and the rod securing portion includes a housing 1730 enclosing a coupling member that includes a sphere 1732 having a cylindrical bore 1734 for engagement with the flexible rod 1702, 1704. The coupling member is capable of allowing translation of the flexible rod 1702, 1704 along the axis of the bore. The coupling member may also optionally allow rotation of the flexible rod about the axis of curvature, about an axis perpendicular to the frontal plane, or about an axis perpendicular to the sagittal plane. In the embodiment depicted in FIGS. 17 and 18, the spinal stabilization system further includes a spring 1740, 1742 disposed around each flexible rod 1702, 1704 to allow for axial damping. FIG. 18 shows a cross-sectional lateral view of the spinal stabilization system taken through the plane of attachment. Although not shown, the springs may be enclosed in a housing or sheathed in a tissue growth-resistant material in order to prevent tissue growth from interfering with their operation. As shown in this figure, the system also includes a disc prosthesis 1750. The illustrative disc prosthesis includes a superior base plate 1752, an inferior base plate 1754 and a central elastomeric insert 1756.

Figure 19:
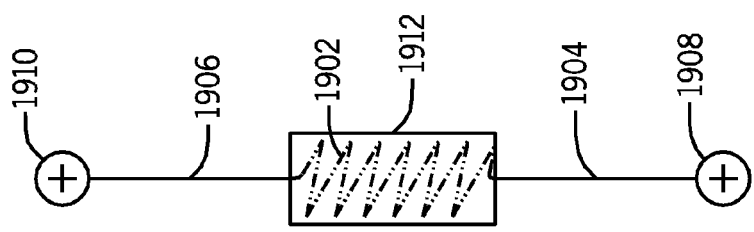
FIG. 19 shows a dynamic stabilizing element composed of a spring protected by a housing.

In a second embodiment, in accordance with this aspect of the invention, the spinal stabilization system includes two dynamic stabilizing elements, wherein each dynamic stabilizing element is composed of a damping element and each damping element is a dynamic bias device as disclosed in U.S. Pat. No. 6,402,750, the disclosure of which is incorporated herein by reference. In this embodiment of the invention, the two stabilizing elements are disposed in a spaced-apart, substantially parallel relation, typically at the posterior of the spine, on opposite sides of the spinous processes. As described in the '750 Patent, the damping elements may be springs, including coiled springs, leaf springs, articulated leaf springs, torsional springs, torsional leaf springs, or articulated torsional leaf springs. Each damping device is connected across a first and a second vertebra by a first and a second connector, respectively. Suitable connectors include screws, hooks and the like. FIG. 19 illustrates a simple damping element, of the type disclosed in the '750 Patent, that may be used as a spinal stabilizing element. This stabilizing element includes a coiled spring 1902 connected to two wires 1904, 1906 which are themselves connected to a first and a second bone screw 1908, 1910. The spring 1902 is housed within a housing 1912 to prevent tissue growth from interfering with the spring 1902.

Figure 20:
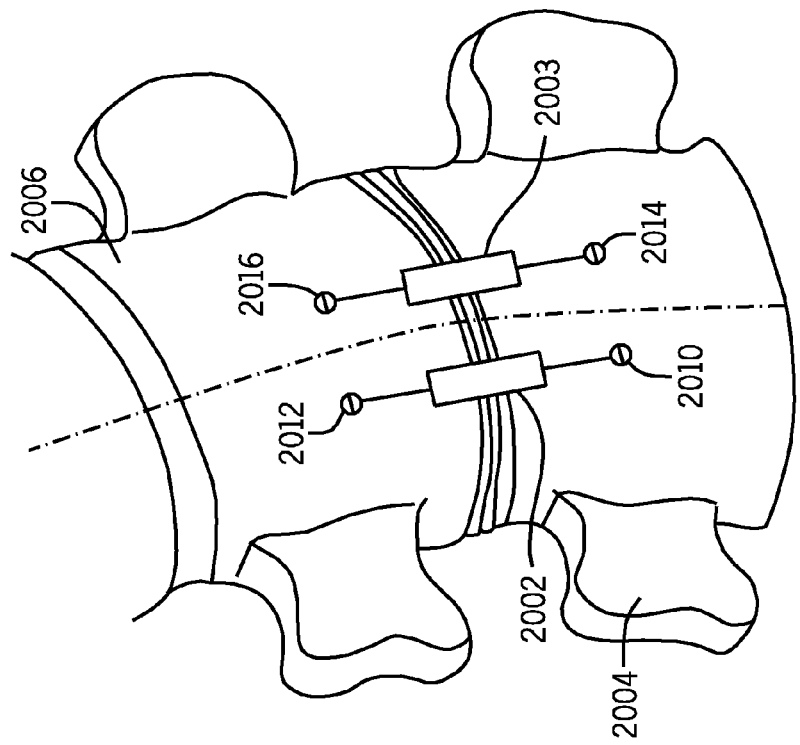
FIG. 20 shows a spinal stabilization system that includes a disc prosthesis and two spinal stabilizing elements of the type shown in FIG. 19 attached to the anterior of a spinal column.
Figure 22:
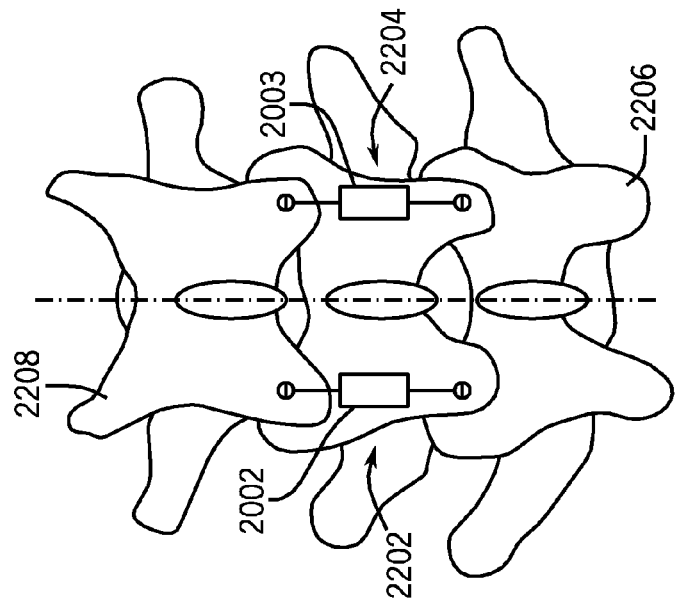
FIG. 22 shows a spinal stabilization system that includes a disc prosthesis and two spinal stabilizing elements of the type shown in FIG. 19 attached across a pair of facet joints.
Figure 21:
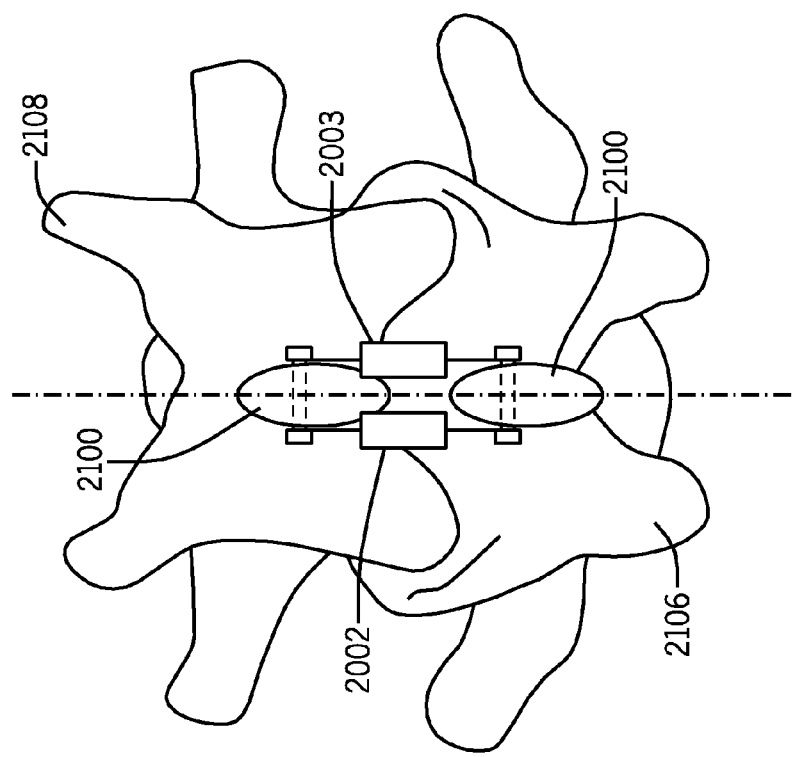
FIG. 21 shows a spinal stabilization system that includes a disc prosthesis and two spinal stabilizing elements of the type shown in FIG. 19 attached to opposite sides of the spinous processes.

FIGS. 20-22 show examples of possible attachment locations for the stabilizing elements of FIG. 19. FIG. 20 shows a first stabilizing element 2002 and a second stabilizing element 2003 attached to the anterior spinal column across a first vertebra 2004 and a second vertebra 2006. The first stabilizing element 2002 is attached to the first vertebra 2004 using a first connector 2010 and to the second vertebra 2004 using a second connector 2012. The second stabilizing element 2003 is attached to the first vertebra 2004 using third connector 2014 and to the second vertebra 2006 using fourth connector 2016.

FIG. 21 and FIG. 22 show two additional possible attachment configurations for the first and second stabilizing elements 2002, 2003 of FIG. 20. In FIG. 21, the stabilizing elements 2002, 2003 are attached to the spinous processes 2100 of two adjacent vertebrae 2106, 2108, symmetrically about the sagittal plane and parallel to the axis of curvature. FIG. 22 shows the two stabilizing elements 2002, 2003 attached across the facet joints 2202, 2204 of two adjacent vertebrae 2206, 2208.

In order to prevent tissue growth from interfering with the moving parts, such as joints or springs, of the stabilizing elements and stabilization system provided herein, it is advantageous to sheath such parts with a tissue-growth resistant material.

The components of the various stabilizing elements and stabilization systems provided herein may be constructed from biologically compatible materials. Many such materials are known. These include, but are not limited to, metals, such as titanium, titanium alloys, chrome cobalt or stainless steel. Other biocompatible materials include graphite and ceramics, such as hydroxapatites. Plastics may also be employed. Suitable plastics include polyethylene (e.g., ultrahigh molecular weight polyethylene) and polyether ester ketone.

The invention has been described with reference to very specific and illustrative embodiments. However, it should be understood that many variations and modifications may be made while remaining within the spirit and scope of the invention.

What is claimed is:

1. A spinal stabilization system, comprising:
  a first flexible rod;
  a first connector, adapted to connect the first flexible rod to a first vertebra in a spinal column in a manner that allows the rod to translate longitudinally with respect to the first vertebra;
  a second connector, adapted to connect the first flexible rod to a second vertebra in the spinal column in a manner that prevents the rod from translating longitudinally with respect to the second vertebra;
  a spring disposed around the first flexible rod between the first and second connectors, wherein the spring is sheathed in a tissue growth-resistant material; and
  a disc prosthesis or disc nucleus replacement disposed between two adjacent vertebrae in the spinal column.

2. The spinal stabilization system of claim 1, wherein the first flexible rod is capable of rotating in at least one direction at the first connector.

3. The spinal stabilization system of claim 1, wherein the first flexible rod is capable of rotating in all directions at the first connector.

4. The spinal stabilization system of claim 1, wherein the first flexible rod is locked from either rotation or translation at the first connector.

5. The spinal stabilization system of claim 1, wherein the first connector comprises a threaded shaft adapted to penetrate a bone and a head having a bore extending laterally therethrough, wherein the bore has a diameter large enough to allow the first rod to translate through the bore.

6. The spinal stabilization system of claim 1, wherein the second connector comprises a pedicle screw, a polyaxial pedicle screw, a lateral mass screw, a hook, or a polyaxial hook.

7. The spinal stabilization system of claim 1, wherein the second connector comprises titanium, titanium alloys, chrome cobalt, stainless steel, graphite, ceramics, hydroxapatites, plastics, polyethylene, ultrahigh molecular weight polyethylene, or polyether ester ketone.

8. The spinal stabilization system of claim 1, further comprising a second bias device, the second bias device comprising:
  a second flexible rod;
  a third connector, adapted to connect the second flexible rod to the first vertebra in a manner that allows the rod to translate longitudinally with respect to the first vertebra;
  a fourth connector, adapted to connect the second flexible rod to the second vertebra in a manner that prevents the rod from translating longitudinally with respect to the second vertebra.

9. A spinal stabilization system, comprising:
  a first damping element having a first end and a second end, the first end adapted to be fixedly connected to a first vertebra in a spinal column and the second end adapted to be fixedly connected to a second vertebra in a spinal column;
  a second damping element having a first end and a second end, the first end adapted to be fixedly connected to the first vertebra and the second end adapted to be fixedly connected to the second vertebra; and
  a disc prosthesis or disc nucleus replacement disposed between two adjacent vertebrae in the spinal column.

10. The spinal stabilization system of claim 9, wherein the first and second damping elements are springs, each spring at the first end having an elongated wire connected to the first vertebra and each spring at the second end having an elongated wire connected to the second vertebra.

11. The spinal stabilization system of claim 9, wherein the springs are selected from the group consisting of coiled springs, leaf springs, articulated leaf springs, torsional springs, torsional leaf springs, or articulated torsional leaf springs.

12. The spinal stabilization system of claim 9, wherein the first damping element and the second damping element comprise at least one of titanium, titanium alloys, chrome cobalt, stainless steel, graphite, ceramics, hydroxapatites, plastics, polyethylene, ultrahigh molecular weight polyethylene, or polyether ester ketone.

13. A spinal stabilization system comprising:
  a stabilizing element comprising:
    a first segment defining a housing in its proximal end, the housing having a ceiling; and
    a second segment comprising a piston extending outwardly from its proximal end, the piston extending into the housing, wherein at least one of the first segment and the second segment comprise a plurality of interconnecting sections coupled end to end;

a damping element disposed in the housing between the piston and the ceiling of the housing, wherein the housing is free of damping fluid;

a first connector adapted to connect the first segment to a first vertebra in a spinal column;

a second connector adapted to connect the second segment to a second vertebra in the spinal column; and a disc prosthesis or disc nucleus replacement disposed between adjacent vertebrae in the spinal column.

14. The spinal stabilization system of claim 13, wherein the damping element is a spring.

15. The spinal stabilization system of claim 13, wherein the damping element is a elastomeric bumper.

16. The spinal stabilization system of claim 13, wherein the first segment and the second segment comprise at least one of titanium, titanium alloys, chrome cobalt, stainless steel, graphite, ceramics, hydroxapatites, plastics, polyethylene, ultrahigh molecular weight polyethylene, or polyether ester ketone.

* * * * *